US008393329B2

(12) United States Patent
Snow et al.

(10) Patent No.: US 8,393,329 B2
(45) Date of Patent: Mar. 12, 2013

(54) PEDIATRIC LUMBAR PUNCTURE POSITIONING DEVICE

(75) Inventors: Marcus H. Snow, Omaha, NE (US); Ken Sieger, Corona, CA (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 13/045,331

(22) Filed: Mar. 10, 2011

(65) Prior Publication Data

US 2011/0214677 A1 Sep. 8, 2011

Related U.S. Application Data

(63) Continuation of application No. PCT/US2009/056528, filed on Sep. 10, 2009.

(60) Provisional application No. 61/191,592, filed on Sep. 10, 2008.

(51) Int. Cl.

| | |
|---|---|
| ***A61G 15/00*** | (2006.01) |
| ***A47B 7/00*** | (2006.01) |
| ***A61F 5/00*** | (2006.01) |

(52) U.S. Cl. ............................. 128/845; 5/621; 606/240

(58) Field of Classification Search .................. 606/237, 606/240; 5/621, 624, 632, 652, 655, 657; 128/845, 846, 869, 870

See application file for complete search history.

(56) References Cited

U.S. PATENT DOCUMENTS

| | | | | |
|---|---|---|---|---|
| 3,933,154 | A | 1/1976 | Cabansag | |
| 4,660,552 | A * | 4/1987 | Latham | 128/878 |
| 5,289,603 | A | 3/1994 | Kumagai | |
| 5,950,627 | A * | 9/1999 | Bologovsky et al. | 128/869 |
| 6,308,712 | B1 * | 10/2001 | Shaw | 128/869 |
| 6,966,087 | B2 | 11/2005 | Robinette | |

OTHER PUBLICATIONS

Written Opinion dated Apr. 29, 2010; email sent to WIPO dated Jun. 3, 2011; email response from WIPO dated Jun. 6, 2011; email sent to ISA/KR dated Jun. 6, 2011; email response from ISA/KR dated Jun. 8, 2011.

* cited by examiner

*Primary Examiner* — Loan Thanh
*Assistant Examiner* — Tarla Patel
(74) *Attorney, Agent, or Firm* — Advent IP, P.C., L.L.O.

(57) ABSTRACT

A device for positioning an infant patient in a clinically preferred position for conducting a lumbar puncture includes a board, a positioning member adjustably coupled to the board, and a locking device coupled to the positioning member for locking the positioning member in a position relative to one or both of the board or the patient. The positioning member may be configured to induce the patient into a clinically preferred position for performing a lumbar puncture on the patient.

8 Claims, 9 Drawing Sheets

PEDIATRIC LUMBAR PUNCTURE POSITIONING DEVICE

CROSS REFERENCE TO RELATED APPLICATION

This application is a continuation of International Application No. PCT/US2009/56528 which claims the benefit of U.S. Provisional Patent Application No. 61/191,592, filed Sep. 10, 2008, entitled A TRANSPORTABLE BOARD FOR THE RESTRAINT OF PEDIATRIC PATIENTS UNDERGOING A LUMBAR PUNCTURE PROCEDURE, which documents are hereby incorporated by reference herein to the extent permitted by law.

BACKGROUND

Lumbar punctures, or spinal taps, are indicated for a variety of reasons. In infants, lumbar puncture is indicated in any infant with symptoms suggestive of meningitis (seizures, intractable vomiting and unexplained fever), and in the evaluation of neonatal intracranial bleeding. The infant must be held firmly in the lateral decubitus or sitting position. Generally, a 22 to 25 gauge needle is inserted into the L3-L4 or L4-L5 interspace. A sample of cerebrospinal fluid is collected for diagnostic testing.

In general, the lumbar puncture procedure is carried out by a physician with the aid of one or more other persons who hold the infant in a side-laying, sitting position with the back arched. This position provides the physician access to the spinal region from which the cerebrospinal fluid will be drawn. Stable, proper positioning of the patient is critical to a successful lumbar puncture. If the patient's back is over-arched, upward pressure can be exerted on the infant's diaphragm resulting in a compromise of the patient's respiratory status. Similarly, neurologic injury or unnecessary trauma can occur if the needle is inserted in the incorrect location.

SUMMARY

Techniques that employ a device configured to position an infant patient in a clinically preferred position for conducting a lumbar puncture are described. In one or more implementations, the device includes a board, a positioning member adjustably coupled to the board, and a locking device coupled to the positioning member for locking the positioning member in a position relative to one or both of the board or the patient. The positioning member is configured to induce the patient into a clinically preferred position for performing a lumbar puncture on the patient.

This Summary is provided solely to introduce subject matter that is fully described in the Detailed Description and Drawings. Accordingly, the Summary should not be considered to describe essential features nor be used to determine scope of the claims.

BRIEF DESCRIPTION OF THE DRAWINGS

The detailed description is described with reference to the accompanying figures. The use of the same reference numbers in different instances in the description and the figures may indicate similar or identical items.

DETAILED DESCRIPTION

Techniques for facilitating a lumbar puncture procedure are described. The techniques employ a device configured to position an infant patient in a clinically preferred position for conducting a lumbar puncture. In one or more implementations, the device includes a board, a positioning device, a board interface, and an inducing device. The board may be any flat, planar base to which a variety of positioning devices may be attached. The instant interface between the board and the patient can be a thin layer of soft material, but the board needs to have sufficient rigidity in order to stabilize the patient during the performance of the procedure. The positioning device is one or more devices that place a patient in a clinically preferred position upon the board. The board interface is the device by which the positioning device may be connected to the board. In some aspects, the board interface is adjustable so that the positioning device can be placed in multiple positions around the board. Lastly, the inducing device is the way by which the system mechanically adjusts the position of the patient into a clinically preferred position. The board and positioning members may comprise an anti-microbial material.

As used herein, a stable, clinically preferred position of the patient facilitates a successful lumbar puncture of an infant patients. As noted above, if the patient's back is over-arched, upward pressure can be exerted on the infant's diaphragm resulting in a compromise of the patient's respiratory status. Similarly, neurologic injury or unnecessary trauma can occur if the needle is inserted in the incorrect location. Accordingly, a clinically preferred position facilitates access to the proper regions of the spine without increased risk of compromising the respiratory status of the patient.

Figure 1:
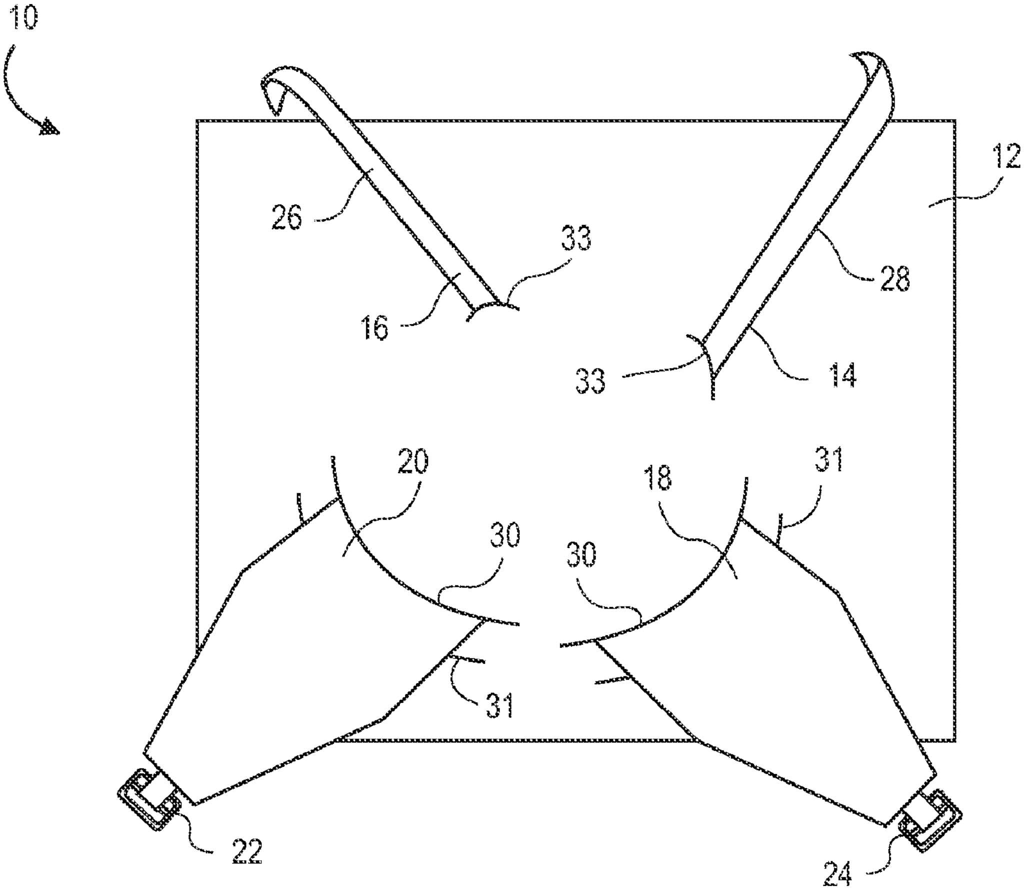
FIG. 1 is top plan view illustrating a lumbar puncture positioning device in accordance with an exemplary implementation of the present disclosure.
Figure 2:
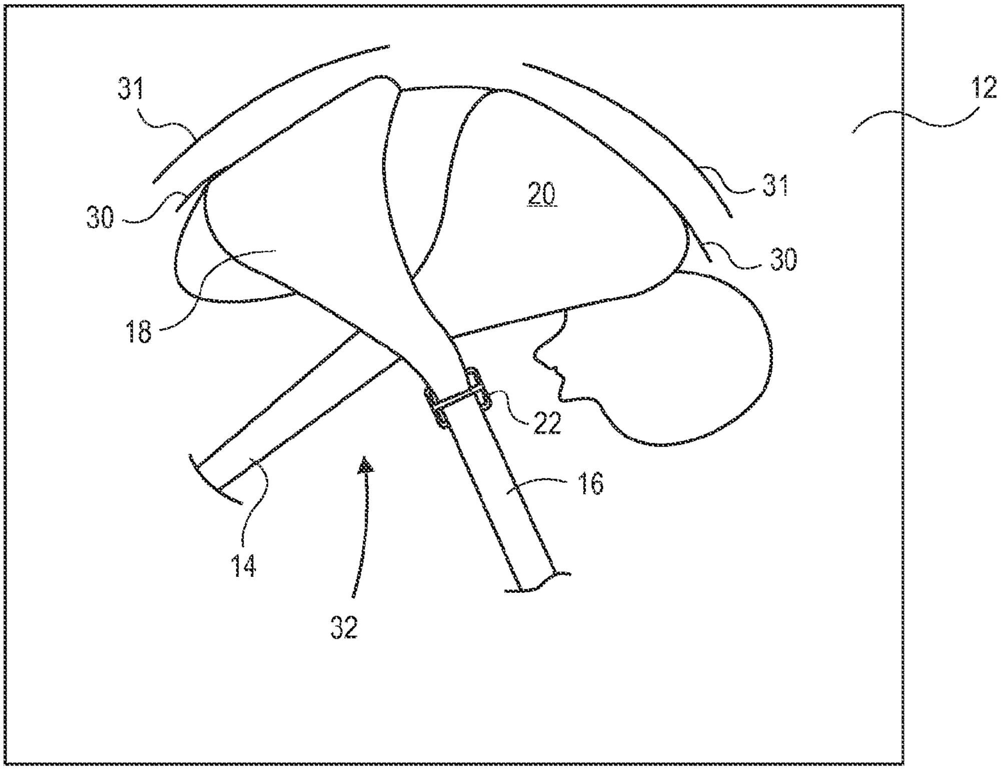
FIG. 2 is another top plan view of the device shown in FIG. 1.
Figure 3:
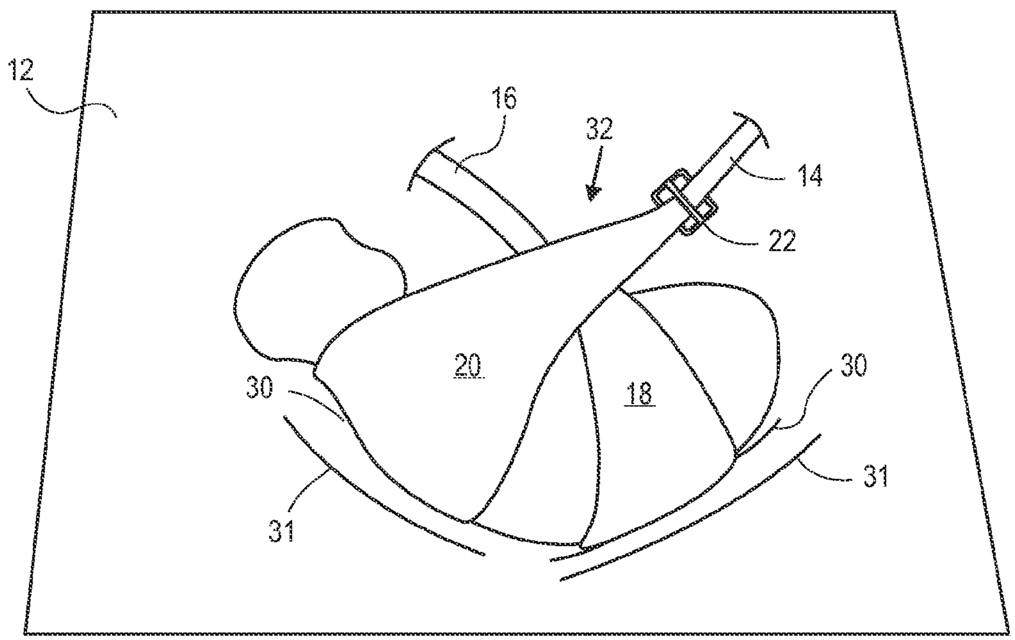
FIG. 3 is a perspective view of the device shown in FIG. 1.
Figure 4:
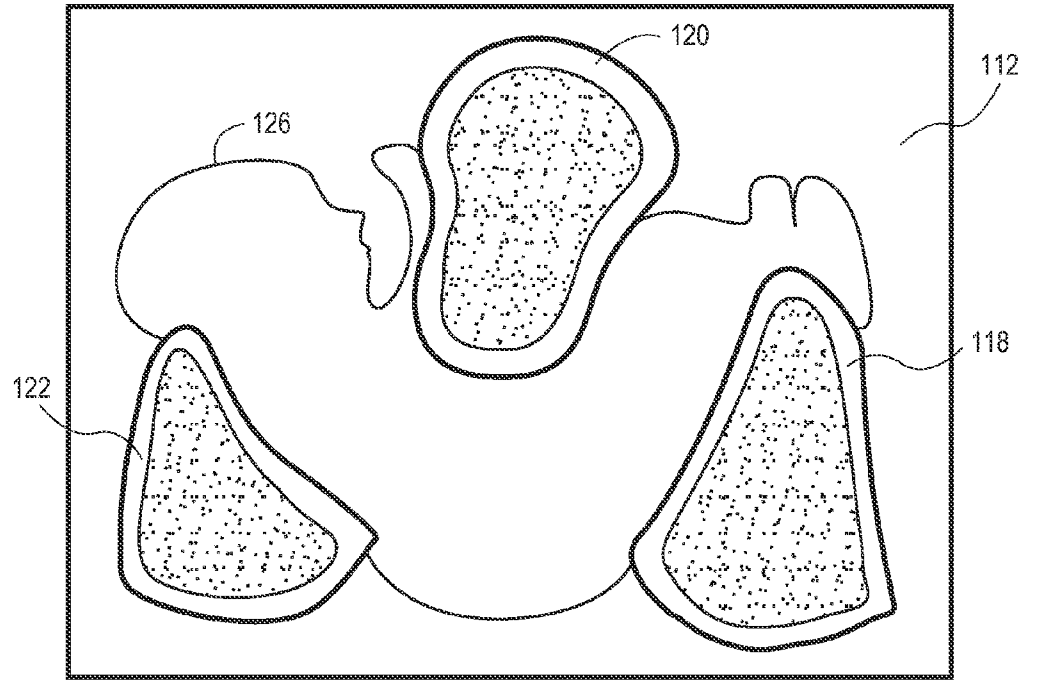
FIG. 4 is a top plan view illustrating a lumbar puncture positioning device in accordance with a second exemplary implementation of the present disclosure.
Figure 5:
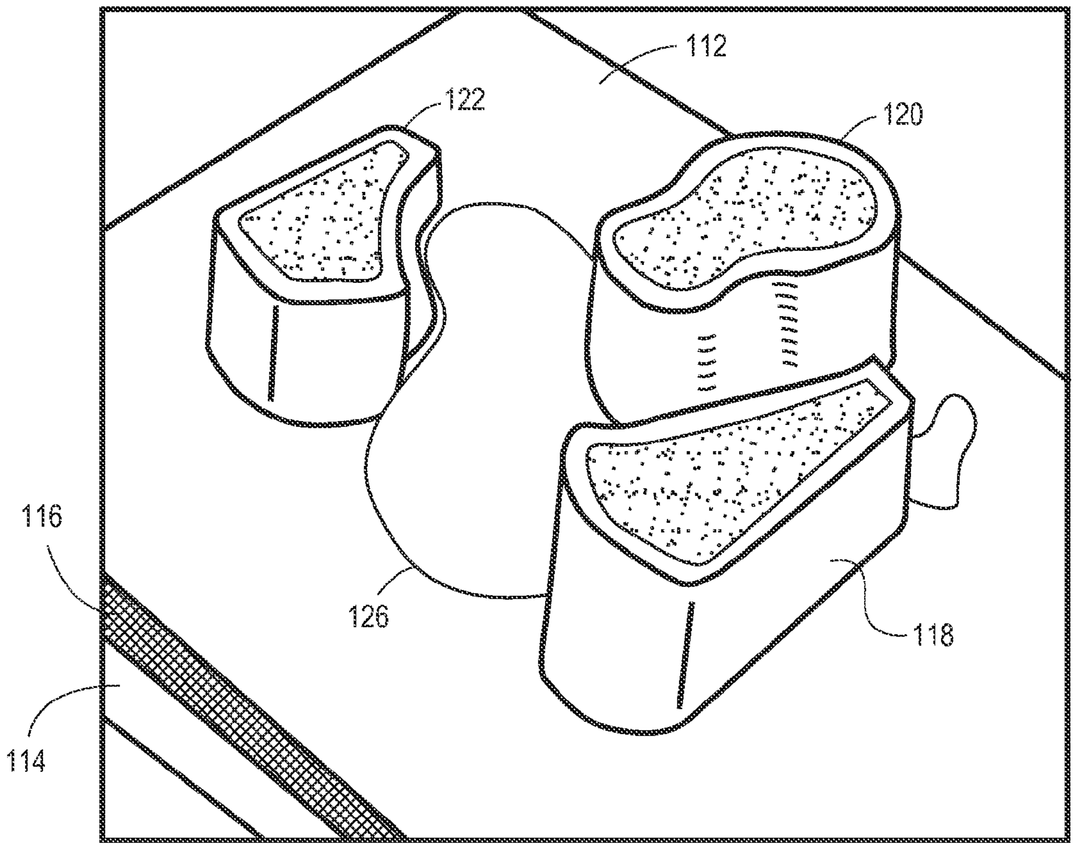
FIG. 5 is a perspective view of the device shown in FIG. 4.
Figure 6:
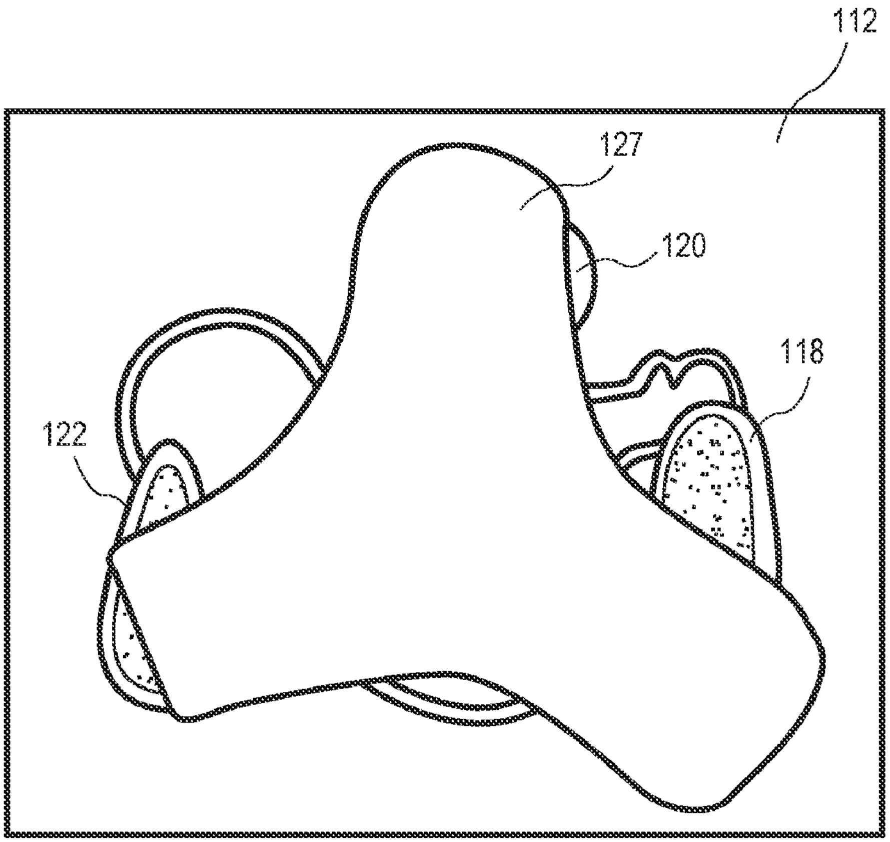
FIG. 6 is a top plan view of the device shown in FIG. 4.
Figure 7:
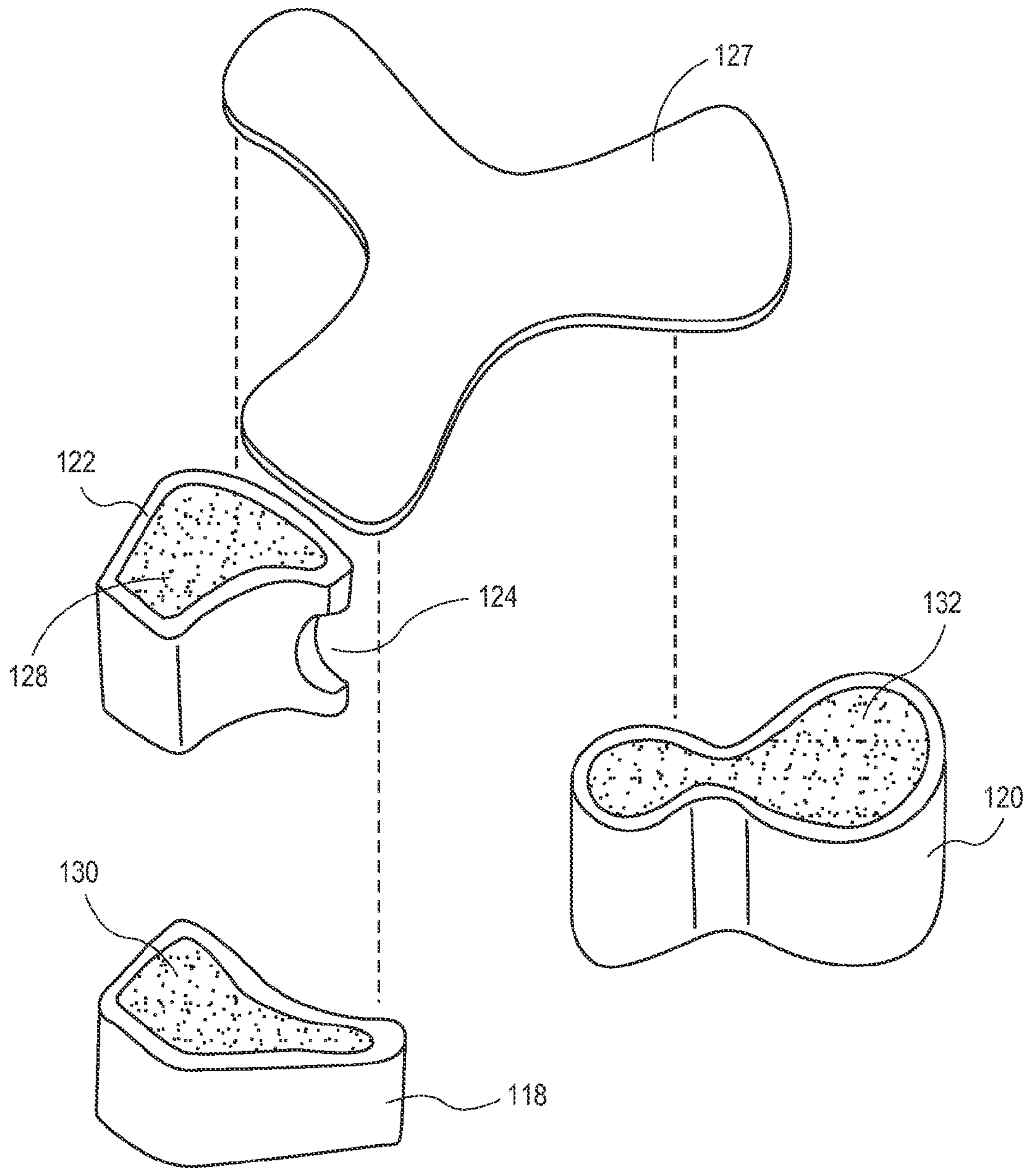
FIG. 7 is a partially-exploded, perspective view of the device shown in FIG. 4.

Referring to FIGS. 1 through 3, an example lumbar puncture positioning device 10 is described. As shown, the device 10 includes a rigid board 12 and a positioning device or positioning members made of straps 14, 16, 18 and 20. Board 12 is primarily composed of a rigid material so that it provides a hard, substantially inflexible base. In one aspect, the board has dimensions of about 12"×18"×24" and is composed of polypropylene. However, a board of any dimensions or material sufficient to contain the other elements of the system and the patient is also contemplated. Board 12 need not be solid or formed of material of sufficient density for repeated use. The board may be formed of thinner and lighter material such that it may be inexpensive and intended for a single use. In some aspects, the board 12 may comprise a plurality of segments that may be separated or folded for storage.

The positioning device is comprised of four straps 14, 16, 18, and 20 which are threaded, fed, or looped through the slits 30 and 33 in the board that serve as the board interface. In one system, the straps are made of Nylon and combine to partially surround the patient's body. The lower back of the patient is uncovered by the straps 14, 16, 18, and 20 so that the operator can access the anatomy needed to perform a lumbar puncture. In some systems, all or substantially all of the positioning device is made of inexpensive materials so that the positioning device can be affordably sold in sterilizable packaging and affordably disposed of after a single use. When positioning the patient, the sterile straps will allow a sterile field around the patient's relevant anatomy.

In the present system 10, the operator feeds each strap comprising the positioning device (18 and 20) through one of the set of board interface slits 30 and 31. Similarly, straps 14 and 16 may be fed through slits 33. In some aspects, the board interface device further comprises an additional anchor for the positioning device: such as a hook and loop attachment, a snap or an adhesive region. The board interface may be adjustable. The straps may also be adjustably positioned by use of hook and loop or other attachment devices for coupling the straps to the board. In the present system, the board interface is comprised of multiple slits 30, 31 at multiple positions on the board 12 so that the straps 14, 16, 18, and 20 can be placed in more than one location and accommodate multiple sizes of patients. In the present system, the straps interface with the board through two sets of slits: one located at the posterior end of the patient and one located behind the neck at the anterior end of the sideways-laying patient. A single strap 18 or 20 is fed through a pair of slits 30 or 31 and anchored to the bottom side of the board 12.

The straps emerging from the posterior slits must be broad enough to cover a substantial amount of the patient's body. The straps taper off along their length into 1 inch straps 26, 28 and a locking device shown as buckles 22, 24. The straps secure the patient by the operation of buckles that arrange the straps diagonally across the patient. The connection of the straps comprising the positioning device induces the patient to assume the clinically preferred position. The straps coordinate to securely position the patient.

In some aspects, the board interface comprises other devices of attaching the straps comprising the positioning device. The Figures depict a board interface comprising four or more slits, but the board interface may accommodate any number of slits so as to maximize adjustability of the positioning device. For example, the alternative slits may be placed in a concentric pattern such that the relative positions for corresponding slits are unchanged. In this manner, the board and straps may accommodate patients of a wide variety of sizes. The operator may anchor the straps to the bottom of the board by a variety of devices before they emerge through the slits. This attachment may occur by clips, snaps, buttons, ties, or loops.

Referring more particularly to FIG. 3, the inducing device 32 is shown as the straps through which tension is applied to the patient through the fastening of the straps 18, 20 to the frontal straps 14, 16. By tightening the buckles between the broad posterior straps 18, 20 and the frontal straps 14, 16, the patient is induced into a clinically preferred position as her shoulders and legs are bent around the point of intersection of the straps. Because the board itself is rigid and exerts an equal, or substantially equal, force back against the straps, the patient is thus effectively held immobile in the clinically preferred position.

Referring to FIGS. 4 through 7, aspects of the system are shown. The board 112 is composed of primary layer 114 of substantially rigid, ridged cross-link closed-cell foam, with a second layer 116 of foam located on top of the primary layer. This second layer 116 of foam may have a laminated hook and loop fastener material (e.g. VELCRO-compatible) fabric top surface. In the present system, the lightweight nature of the foam board 112 increases the portability and versatility of this device. The foam also makes the material less expensive to produce and single use or limited use disposability affordable. The board may be formed to the dimensions described in the previous Figures but, the board can be formed to any dimension that accommodates the placement of the positioning device.

In the present system, the positioning device or positioning members are comprised of three separate foam blocks 118, 120, and 122. In some aspects, these blocks are composed of anti-microbial foam, though all clinically acceptable types of foam or other suitable material are contemplated. Preferably, the foam has a minimum density of 1.7 lbs/ft$^3$, a SAG Factor of at least 2.0, permits air flow of no more than 4.0 ft$^3$/min, a tear strength of at least 2.0 lbs/linear inch, a tensile strength of 10.0-15.0 lbs/in$^2$, elongation of 125-175%, resilience of at least 30% and Compression Set 90%, for 22 hours at 158° Fahrenheit of less than 10%. As with the prior Figures, the positioning device is formed of materials that can be packaged in single use sterile packaging and produced affordably enough to be affordably disposable. When the sterile foam blocks position the patient, they create a sterile field around the anatomy to perform the lumbar puncture.

Together, the positioning device is comprised of foam blocks that surround the patient and induce the patient into a clinically preferred position. The first block 120 (hereinafter the "Pivot Block") is a foam block, shown as configured in the shape of an "8", but any shape that will induce the patient into a clinically preferred position when appropriately interfaced with the board may be used. The Pivot Block's 120 round edge allows inducement of the patient to curl around the Pivot along their ventral side. In some aspects, for infant lumbar puncture, the Pivot Block 120 is about 4.5" tall, but other heights that correspond to the width of the patient are permissible. Additionally, the system may comprise a kit containing a number of Pivot Blocks in order to accommodate patients of a variety of sizes. The second block 122 (hereinafter the "Head Block") is a foam block that is comprised out of substantially the same material as the Pivot Block 120 but formed to a different shape. In some aspects, the Head Block 122 contains a groove 124 for supporting the neck of the patient, which specifically supports neck flexion at a clinically recommended level. The third block 118 (hereinafter the "Lower Block") is a foam block that is comprised out of substantially the same material as the Pivot Block 120 and Head Block 122 but formed to a different shape. Because the Lower Block 118 is not required to induce the patient to conform to a particular position or support critical anatomy, the Lower Block 118 need not conform to a specific shape. Instead, Lower Block 118 provides a guide to position the patient's lower body in the clinically preferred position.

Conjunctively, the blocks 118, 120, and 122 are arranged on the board such that when a patient is placed between them, the patient must automatically assume a clinically preferred position. In some aspects, the board 112 has markings 126 which assist with placement of the blocks into the correct formation. Specifically, the Pivot Block 120 is placed in the center of the board, or any location where the subsequent blocks and the patient may be properly placed in relation thereto. The patient is then placed on the board and assumes the clinically preferred position by curling around the Pivot Block 120. The Lower Block 118 is then placed behind the patient's legs, thereby compressing them between the Pivot Block 120 and the Lower Block 118 in the clinically preferred position. The Head Block 122 is then placed around the patient's upper body, taking care to ensure that the patient's neck is placed into the neck groove 124. In this manner, the patient is conformed to the clinically preferred position.

In some aspects, the foam blocks 118, 120 and 122 comprising the positioning device are formed from a deformable material that can be packaged inside an airtight package wherein the package can be vacuum sealed so that the packaged foam blocks are substantially smaller. Further, the board 112 may be formed from multiple components or otherwise jointed so that it can be folded or assembled from smaller pieces. In some aspects, both the positioning device and the board are packaged in containers small enough to ship as part of a lumbar puncture tray: such as a Covidien SENSI-TOUCH™ Lumbar Puncture Tray with Safety Components. For example, for systems where the positioning device is one or more straps, the straps and board 112 can be folded to fit on top of the tray. In such systems, the board 112 and the positioning device can be formed out of materials commonly used to make disposable medical devices.

The board interface may be comprised of VELCRO hooks which are attached to both the top and bottom of the Pivot Block 120, Head Block 122, and Lower Block 118, along with the VELCRO-compatible fabric used as the top surface of the board. In some aspects, the SCOTCHMATE—SJ3526N or SJ3527N family of nylon hooks and loop reclosable fasteners may be used. The board interface comes into play when the various blocks are placed in their appropriate positions upon the board.

In some aspects, induction to the clinically preferred position is aided by Locking Strip 127. Locking Strip 127 is shown as a piece of VELCRO-compatible fabric, formed to outline the profile of the positioning device. The Locking Strip 127 interfaces with the foam blocks comprising the positioning device. To facilitate the induction of the patient into the clinically preferred position, the operator secures the Locking Strip 127 firmly to the VELCRO-top 128 of the Head Block 122. Next, the Locking Strip 127 is stretched taught down to the Lower Block 118 and is firmly secured via its VELCRO-covered top 130. Finally, the Locking Strip 127 is stretched over the patient's body to the Pivot Block 120 until a moderate degree of tension is acquired. The Locking Strip 127 is then firmly secured to the VELCRO-compatible top 132 of Pivot Block 120 in a manner similar to the Head Block 120 and Lower Block 118, thus effectively securing the blocks around the patient and into an immobile structure which insures that the patient cannot shift out of the clinically preferred position while blocks 118, 120, and 122 and Locking Strip 127 are in place.

Figure 8:
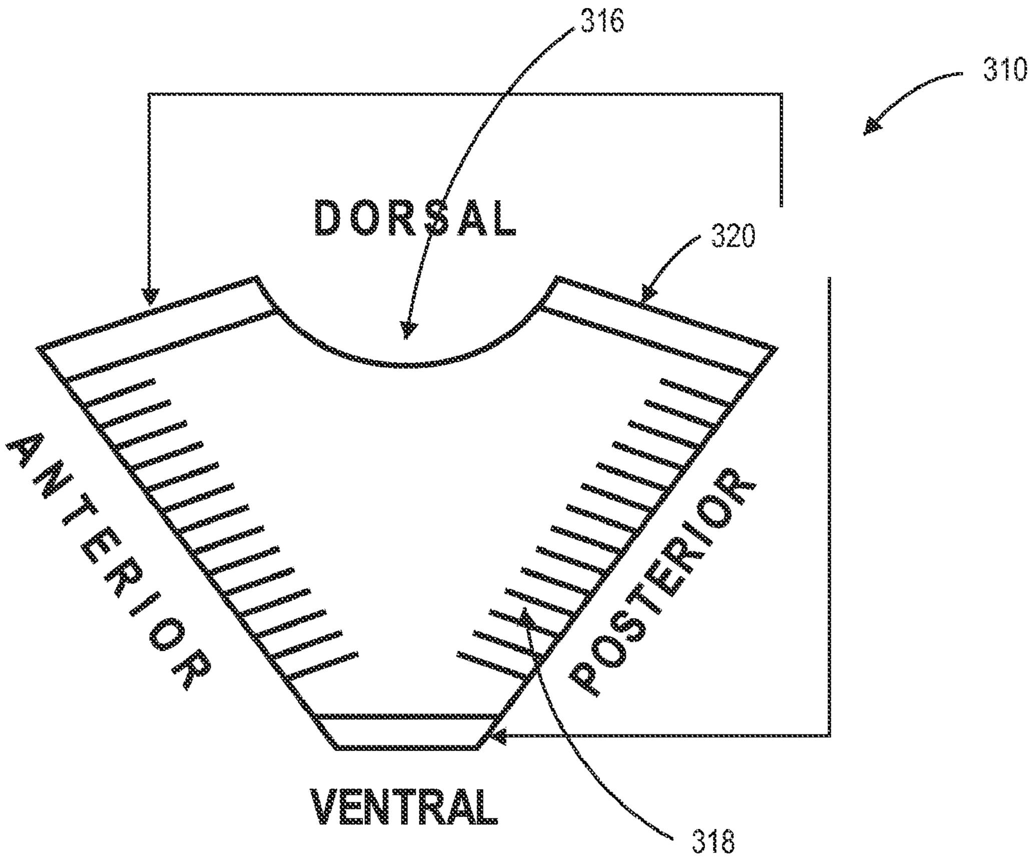
FIG. 8 is an elevation view of part of a lumbar puncture positioning device in accordance with the present disclosure.
Figure 9:
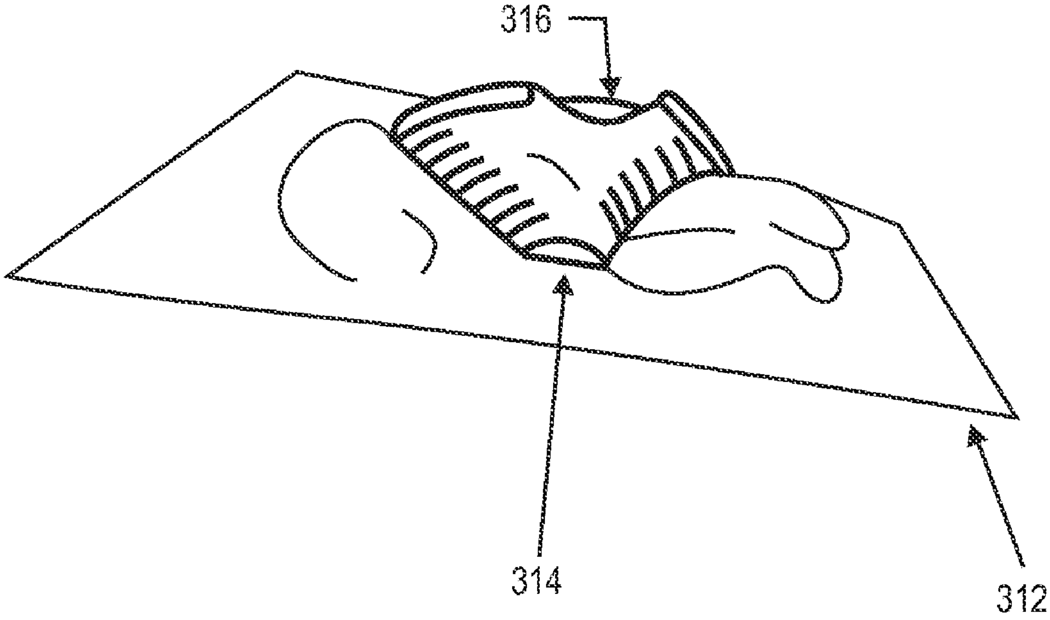
FIG. 9 is a perspective view of the device shown in FIG. 8 in use with a patient.

Referring to FIGS. 8 and 9, another aspect is shown. The positioning device or positioning member may be primarily comprised of single device 310 that surrounds the patient to form a continuous point of contact. The positioning device further includes elements that support the patient and induce the patient to assume a clinically preferred position.

As with prior described systems, the positioning device interfaces with the board 312 at an interface 314. For some aspects, utilizing a rigid board, the board interface comprises straps or ties that are permanently attached to the positioning device. The straps may interface with the board by secured insertion through one or more holes or slits in the board that allow for the adjustment of the positioning device to accommodate and position variable patients. For some aspects that utilize a foam board with a fabric surface, the board interface 314 may be a VELCRO or other hook and loop element that will engage with the softer surface of the board as in the previous aspects.

In the present system, the positioning device can be a woven device. The woven device must be able to non-traumatically restrain the patient and be able to flexibly accommodate the patient when the device is pulled over the patient. The woven device could be formed of any variety of materials. A non-woven positioning device may similarly surround the patient utilizing a continuous point of contact. Given the continuous point of contact formed by the positioning device in the present device, the positioning device may be further formed to contain a window 316 so that the operator has access to the patient's lower back in order to perform the procedure.

Indicative of the present system is that the single device may constitute the positioning device and simultaneously serve as the support device and the inducing device. Several elements of the positioning device facilitate this multiple purpose. For example, where the single device is a woven device, it may be formed to have anterior, posterior, dorsal and ventral sides. The anterior and posterior sides are formed to contain elastic elements 318 so as to exert force on the patient and induce a clinically preferred position for a lumbar puncture. The positioning device can include additional elastic elements to help induce the clinically preferred position.

The ventral and dorsal sides of the positioning device further include semi-rigid pads 320 to leverage the force exerted by the elastic elements 318 and facilitate the induction of the clinically preferred position. The semi-rigid pads 320 also help the single device to support the patient as well. The continuous point of contact utilized in the present system provides generally equal support over the patient's entire body. The semi-rigid pads 320 provide increased support to select areas of the patient's body.

The support pads may define the lumbar access area. Further aspects may utilize non-woven single device positioning device or different materials to adjust the relative support over the patient's body. The present system envisions the utilization of different materials, tension of elastic elements, and inclusion of pads and other elements to support and induce the correct position of the patient.

Although techniques for performing a lumbar puncture procedure have been described in language specific to structural features and/or methodological acts, it is to be understood that the appended claims are not necessarily limited to the specific features or acts described. Rather, the specific features and acts are disclosed as exemplary forms of implementing the claimed devices and techniques.

What is claimed is:

1. A device for positioning an infant patient for conducting a lumbar puncture comprising:

a board configured to support the infant patient lying on its side;

a positioning member comprising a plurality of blocks configured to be attached to the board, the plurality of blocks including a head block configured to support the neck of the infant patient, a lower block configured to position the lower body of the infant patient, and a pivot block configured to induce the infant patient into a decubitus position wherein the back of the infant is arched to facilitate a lumbar puncture at the L3-L4 interspace or the L4-L5 interspace;

a locking device coupled to the positioning member for locking the positioning member in a position relative to one or both of the board or the patient;

wherein the positioning member is configured to induce the infant patient into a clinically preferred position for performing a lumbar puncture on the infant patient.

2. The device as recited in claim 1, wherein the plurality of blocks are configured to be positioned on the board and attached to the board via hook and loop fastener material, the hook and loop fastener material applied to a surface of each of the plurality of blocks and to a surface of the board.

3. The device as recited in claim 1, wherein the board comprises markings configured to facilitate positioning of one or more of the plurality of blocks.

4. The device as recited in claim 1, further comprising a locking strip configured to interface with the plurality of blocks to secure the plurality of blocks around the infant patient.

5. A method for performing a lumbar puncture procedure comprising:

positioning an infant patient in a device comprising:

a board configured to support the infant patient lying on its side;

a positioning member comprising a plurality of blocks configured to be attached to the board, the plurality of blocks including a head block configured to support the neck of the infant patient, a lower block configured to position the lower body of the infant patient, and a pivot block configured to induce the infant patient into a decubitus position wherein the back of the infant is arched to facilitate a lumbar puncture at the L3-L4 interspace or the L4-L5 interspace;

a locking device coupled to the positioning member for locking the positioning member in a position relative to one or both of the board or the patient;

puncturing the patient in the spinal region; and extracting a sample of cerebrospinal fluid.

6. The method as recited in claim 5, further comprising a locking strip configured to interface with the plurality of blocks to secure the plurality of blocks around the infant patient.

7. A kit comprising:

a board configured to support an infant patient undergoing a lumbar puncture procedure lying on its side;

a positioning member comprising a plurality of blocks configured to be attached to the board, the plurality of blocks including a head block configured to support the neck of the infant patient, a lower block configured to position the lower body of the infant patient, and a pivot block configured to induce the infant patient into a decubitus position wherein the back of the infant is arched to facilitate a lumbar puncture at the L3-L4 interspace or the L4-L5 interspace; and a locking device coupled to the positioning member for locking the positioning member in a position relative to one or both of the board or the patient.

8. The kit as recited in claim 7, further comprising a locking strip configured to interface with the plurality of blocks to secure the plurality of blocks around the infant patient.

* * * * *

UNITED STATES PATENT AND TRADEMARK OFFICE

CERTIFICATE OF CORRECTION

PATENT NO. : 8,393,329 B2
APPLICATION NO. : 13/045331
DATED : March 12, 2013
INVENTOR(S) : Snow et al.

It is certified that error appears in the above-identified patent and that said Letters Patent is hereby corrected as shown below:

The Title page, Item No. (75), delete "Ken Sieger" and insert -- Ken Siegner --, therefor.

Signed and Sealed this
Twenty-first Day of May, 2013

Teresa Stanek Rea
*Acting Director of the United States Patent and Trademark Office*